(12) United States Patent  
Parker et al.

(10) Patent No.: US 6,497,649 B2
(45) Date of Patent: Dec. 24, 2002

(54) ALLEVIATING MOTION, SIMULATOR, AND VIRTUAL ENVIRONMENTAL SICKNESS BY PRESENTING VISUAL SCENE COMPONENTS MATCHED TO INNER EAR VESTIBULAR SENSATIONS

(75) Inventors: Donald E. Parker; Been-Lirn Henry Duh; Thomas A. Furness; Jerrold D. Prothero; Eric J. Seibel, all of Seattle, WA (US)

(73) Assignee: University of Washington, Seattle, WA (US)

( * ) Notice: Subject to any disclaimer, the term of this patent is extended or adjusted under 35 U.S.C. 154(b) by 74 days.

(21) Appl. No.: 09/766,144

(22) Filed: Jan. 21, 2001

(65) Prior Publication Data

US 2002/0099257 A1 Jul. 25, 2002

(51) Int. Cl.$^7$ .............................................. A61M 21/00
(52) U.S. Cl. ..................................................... 600/27
(58) Field of Search .................... 600/27, 28; 702/150, 702/153, 154, 173, 175, 176

(56) References Cited

U.S. PATENT DOCUMENTS

| | | | | |
|---|---|---|---|---|
| 4,576,184 A | * | 3/1986 | Westerman | 600/546 |
| 4,925,878 A | * | 5/1990 | Bodo et al. | 514/646 |
| 5,042,910 A | * | 8/1991 | Dolezal | 2/428 |
| 5,067,941 A | * | 11/1991 | Hendricks | 600/27 |
| 5,629,848 A | * | 5/1997 | Repperger et al. | 340/963 |
| 5,647,835 A | * | 7/1997 | Martineau | 128/898 |
| 5,694,939 A | * | 12/1997 | Cowings | 128/671 |
| 5,829,446 A | * | 11/1998 | Tiffany | 128/898 |
| 5,966,680 A | * | 10/1999 | Butnaru | 702/150 |
| 6,050,822 A | * | 4/2000 | Faughn | 345/952 |
| 6,228,021 B1 | * | 5/2001 | Kania | 128/897 |
| 6,234,953 B1 | * | 5/2001 | Thomas et al. | 600/14 |

* cited by examiner

Primary Examiner—Teresa Walberg
Assistant Examiner—Daniel Robinson
(74) Attorney, Agent, or Firm—Ronald M. Anderson

(57) ABSTRACT

Display of an independent visual background provides a visual reference corresponding to the perceptions of a person's vestibular system, thereby substantially reducing or eliminating motion sickness that otherwise occur due to a mismatch between the visual perception of motion or non-motion and the sensations of the vestibular system. If the person is wearing a head-mounted display (HMD), is in motion, or is in a moving environment, a motion tracking system or other motion sensors are employed to produce signals indicative of the motion of the environment and/or of the person. The signals produced are then processed using a vestibular model, producing a modified signal corresponding to the perception of motion by the person's vestibular system. Using this modified signal, the independent visual background is displayed to the user, providing a visual reference that corresponds to the perception of the vestibular system. If the person is in a fixed environment and watching a moveable or moving display, the IVB can either be included on the image or in a peripheral area around the display. The perceptibility of the IVB can be adjusted by the observer to minimize its distracting impact on a visual task, while ensuring that it is sufficiently perceptible to avoid motion sickness.

39 Claims, 10 Drawing Sheets

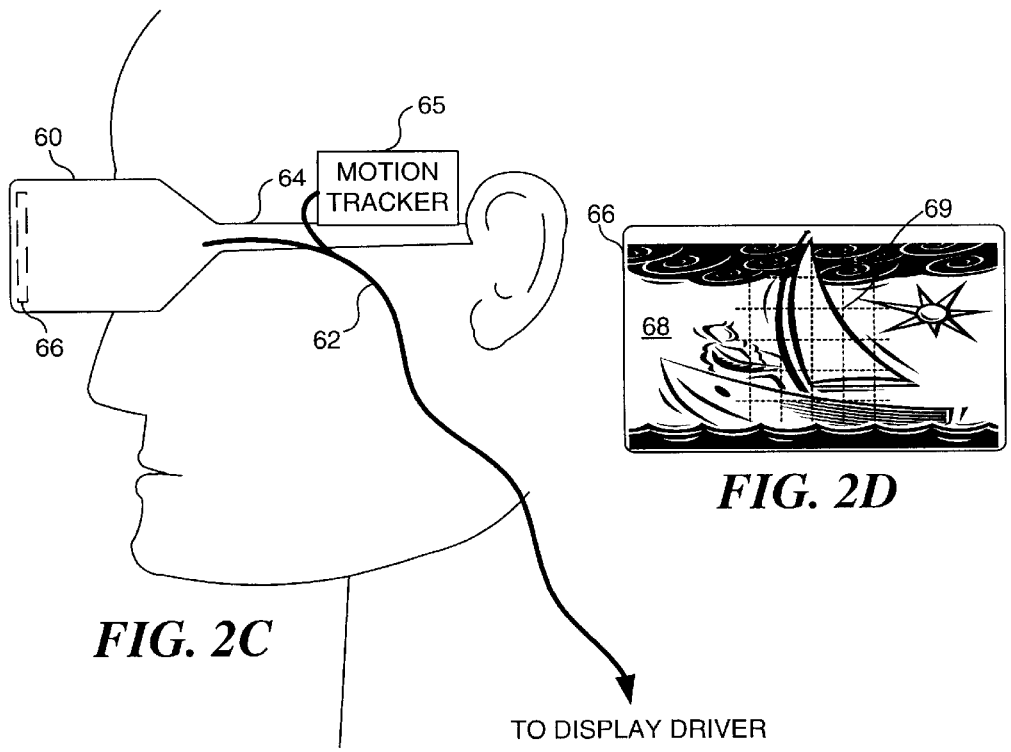
FIG. 2C
FIG. 2D
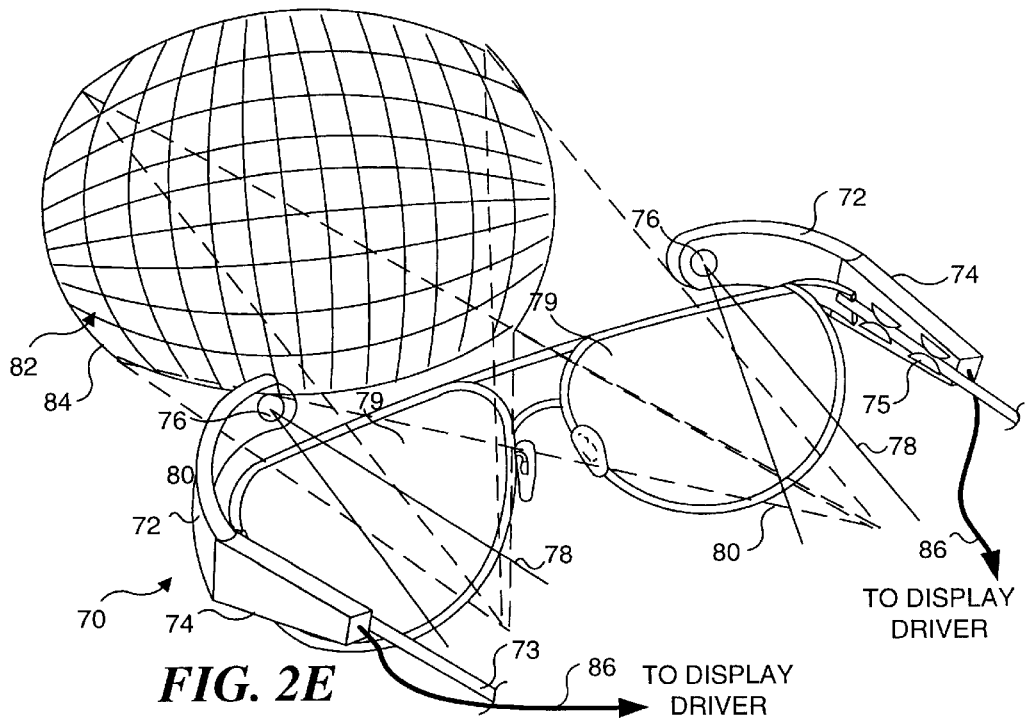
FIG. 2E

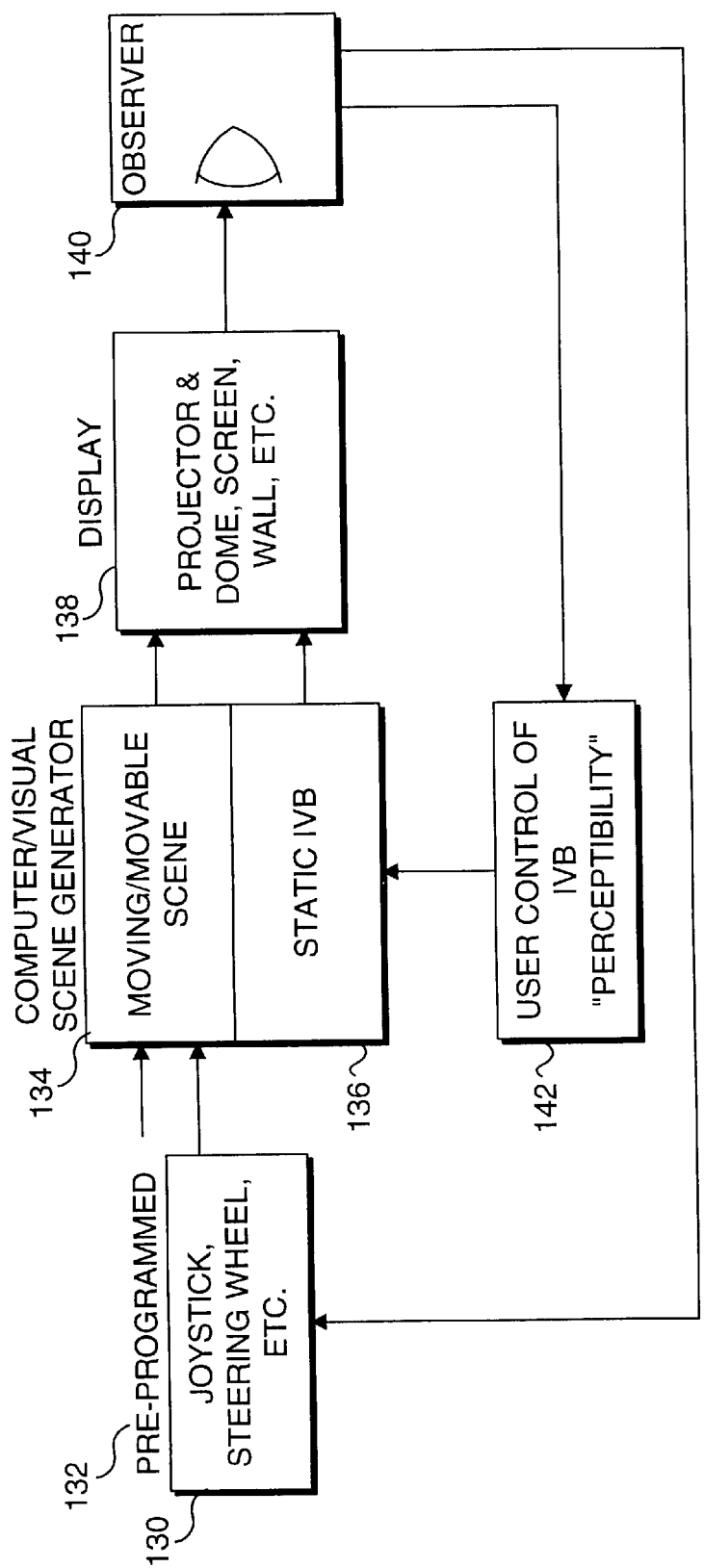

ALLEVIATING MOTION, SIMULATOR, AND VIRTUAL ENVIRONMENTAL SICKNESS BY PRESENTING VISUAL SCENE COMPONENTS MATCHED TO INNER EAR VESTIBULAR SENSATIONS

FIELD OF THE INVENTION

The present invention generally relates to the use of a visual reference to prevent apparent motion sickness caused by conflicting sensed cues, and more specifically, to a method and apparatus that visually indicate a background reference corresponding to the vestibular senses of the inner ear.

BACKGROUND OF THE INVENTION

A problem commonly experienced by people traveling in a vehicle, aircraft, or boat is motion sickness. Motion sickness occurs because of a mismatch between the sensations felt in the inner ear vestibular system and those experienced through other senses, such as a person's visual perceptions. It should be noted that for purposes of this discussion and as used in the claims that follow, it will be understood that the vestibular system of the inner ear is an "inertial motion sensor." Balance receptors in the inner ear respond to gravity (e.g., changes in orientation), velocity, and changes in velocity (accelerations) experienced while moving. When the sensations experienced by the inner ear fail to match visual cues, motion sickness often results.

For example, a passenger traveling along a winding road in an automobile experiences linear and angular accelerations each time the vehicle travels around a curve. The response of the vestibular sensing system to the acceleration caused by the motion of the vehicle will not match the visual perception unless the person is continually viewing the road so that the perception of the person's inner ear corresponds to the visually perceived path of the vehicle around curves. It is for this reason that the driver of a vehicle normally does not experience motion sickness, even though motion sickness may result when the person is traveling as a passenger in the vehicle driven along the same road and in the same manner, by someone else. A driver continuously watches the road and visually perceives the motion of the vehicle so that the visual perceptions match the senses of the inner ear. Passengers in a vehicle, who are reading, or only viewing the interior of the vehicle, or carrying on other activities that cause them not to watch the road, will have a visual perception that does not match the senses of their inner ear. As a consequence, the passengers may experience symptoms associated with motion sickness, such as nausea, headache, and disorientation. Most people find that while traveling as a passenger, they can generally avoid motion sickness by watching the road as if they were driving the vehicle, so that their visual input more closely matches the sensations of their vestibular system. However, when confined within an interior cabin of a ship or in other situations in which the actual movement of the person experienced by the vestibular inner ear apparatus cannot readily be related to the visual perception of that movement, motion sickness is not so easily avoided.

The equivalent of motion sickness can also be experienced when a person is not moving, but the visual input experienced by the person appears to indicate that the person is moving. When a person is in an earth-fixed, and non-moving environment, the mismatch between an apparent self-motion that is evoked visually and the sensation by the inner ear indicating that no environment motion is actually being experienced can cause the symptoms of motion sickness. The conditions leading to this problem can occur, for example, when viewing an IMAX™ motion picture presentation (i.e., a movie displayed on a wrap-around screen) in which motion is portrayed, or when participating in a flight or driving simulation running on a computer, or when viewing moving images in an artificial environment produced with a head-mounted display (HMD). Accordingly, as used throughout this disclosure and in the claims that follow, the term "motion sickness" is intended to encompass any of the symptoms commonly associated with being in a moving environment, as noted above, as well as corresponding symptoms experienced by persons who are not moving, but are exposed to a virtual environment in which motion is displayed, causing the perception of motion by the person.

The unpleasantness associated with motion sickness during travel can be sufficient to cause a person to refuse to travel under the conditions that produce motion sickness. Similarly, the motion sickness that can result when interacting in a simulator or viewing a virtual environment presentation may preclude a person from viewing a presentation on a surround screen or from participating in a simulator or virtual environment experience. It would be unfortunate, when such visually stimulating experiences are becoming more readily available and more refined due to advances in graphics and display technology, that concern about motion sickness might prevent someone from enjoying these experiences. Accordingly, a solution is needed that will enable a person to participate in activities where visual scene motion may evoke illusory self-motion without concern that the symptoms of motion sickness will be felt, or at least, that the severity of such symptoms can be controlled. Ideally, any solution that avoids these symptoms should also be applicable to preventing actual motion sickness caused when a person is in motion, as described above.

Recognizing that motion sickness is caused by a sensory mismatch, a solution purportedly addressing this problem is described in U.S. Pat. No. 5,966,680 (Butnaru). This patent discloses the use of a display on which "an artificial labyrinth" is presented. The artificial labyrinth is displayed in an HMD or as a projection onto the retina and comprises an array of lines that are controlled to indicate movement of the user's head in regard to a baseline position. The reference teaches that this indication should be updated at least every 150 ms. The artificial labyrinth includes visual cues that show changes in roll, pitch, yaw, and elevational position of the user's head. To sense these changes in position, head-mounted gyroscopic, accelerometers, or magnetostrictive sensors are employed. The signals produced by the sensors are input to a microprocessor that controls the display of the visual cue lines directly in response to the sensor output signals. The patent also teaches that a global positioning satellite (GPS) receiver can be included to provide an orientation or location signal that is visually presented to a user. The cue lines indicative of the user's orientation relative to the baseline are displayed on transparent lenses of an HMD, or projected onto corrective or plain lenses of glasses, or projected into space a few feet in front of the user as a holographic display, or projected onto the retina of the user.

Alternatively, the Butnaro patent teaches that a camera and a projector can both be mounted on a glasses frame worn by the user and used to produce a recorded image of a scene in front of the user. The recorded image is conveyed to a microprocessor and averaged with other images produced by the camera to produce a slowly changing display of the user's environment. The slowly changing display is projected onto the lenses of the glasses, so that the user only perceives the averaged image as displayed by the projector on the inner surface of the lenses. The patent also indicates that a less desirable technique senses orientation with sensors that are not mounted to the user, but are instead responsive to the orientation of an environment (such as an automobile, aircraft, or boat) in which the user is traveling.

There is a substantial problem with the solution proposed by Butnaro to prevent motion sickness. Butnaro teaches that the signals produced by head-mounted accelerometers or other motion sensors are directly indicative of the observer's true orientation and motion and thus, that these signals correspond to the sensations of the inner ear. Butnaro apparently fails to fully appreciate that some motion tracker sensors do NOT produce signals indicative of the true orientation and motion to which the devices are subjected. For example, accelerometers do not sense true constant linear or angular velocities, whereas an inertial tracker may do so. Butnaro apparently fails to fully appreciate that the response of the vestibular receptors to motion does NOT correspond to that of head-mounted accelerometers or other motion sensors. As will be clear from the discussion that follows, tracker/accelerometer signals must be manipulated appropriately so that simulated vestibular signals match real ones. Finally, Butnaro apparently fails to fully appreciate that the response of the vestibular receptors often does NOT reflect the true orientation and motion of a person's head and body. Indeed, it is very possible that a mismatch between the visual cues provided by the Butnaro system and the perceived sensations of a user's vestibular system might tend to cause motion sickness rather than prevent it. For example, a person may be learning a task in a simulation while in a moving environment such as a car, airplane, or centrifuge. Butnaro proposes to provide a visual reference that matches the person's true orientation and motion. However, if the real angular motion exceeds the vestibular semicircular canal long time constant (as further discussed below), the vestibular signal will indicate that the person is stationary. Presentation of a visual reference indicating the true rotational motion of the person would be in conflict with the perception of that person's vestibular receptors, and this conflict between the vestibular perception and Butnaro's visual reference would be likely to exacerbate rather than alleviate motion sickness. The rotating environment case may be an extreme example, but nevertheless illustrates the fundamental issue with the disclosure of this prior art patent. More subtle cases illustrating problems with the reference are associated with time delays and phase shifts between tracker signals and vestibular perception. Time delays and phase shifts are known to evoke motion sickness.

Another example to illustrate discrepancies between vestibular perception and true motion is otolith ambiguity. This ambiguity can occur because the sensation of the otolith organs (in the inner ear) may reflect either linear acceleration or head tilt with respect to gravity. The ambiguity is apparent in the illusion of upward pitch experienced by pilots during forward linear acceleration in higher performance aircraft. The system disclosed by Butnaro would not take this ambiguity into account.

It would therefore be preferable to provide visual cues that truly match the perceptions of the vestibular organs, even though to do so may require that a signal indicative of the actual physical motion and acceleration experienced by a user be modified in accord with a vestibular model, to correspond to the true perceptions of the vestibular system. Also, it is possible that the model may need to be refined to achieve optimum results. For example, it may also be necessary to compensate for the affects of aging or other variability in the perceptions of users when providing a visual reference that corresponds to the sensations of the inner ear for a specific person. For this reason, any system and model attempting to match a visual perception with the perception of the vestibular organs should be capable of reprogramming and refinement to fine tune the match between the visual cues and the perceived motion by the person's vestibular system. Butnaro's disclosed invention does not have the capability of providing such compensation or modifying the visual cues to account for differences between individuals.

In addition, the invention disclosed in the above-referenced Butnaro patent is unlikely to be of significant benefit if the user is in an earth-fixed environment where visual scen motion causes the person to feel that he/she is moving, such as can occur when viewing a surround screen motion picture presentation, or when viewing and participating in a driving/flight simulator or virtual environment display. Also, it is probably impractical to require a user to continually wear an HMD or other display device while traveling for an extended period of time. In some cases, it will be preferable to provide an independent visual background (IVB) providing the required visual cues that are projected onto an interior surface of a cabin of a boat or other conveyance, or which is included in a surround presentation or in the background on a display so as to provide a visual reference corresponding to the perception of a person's inner ear vestibular system. One advantage of such an IVB reference is that a plurality of people to which the display surface is visible will all benefit from viewing the reference.

Another problem with Butnaro and other prior art techniques that attempt to provide a visual reference to avoid motion sickness is that the visual reference can be too distracting. For example, in the technique disclosed in the Butnaro patent, it is clear that the cue lines must be very perceptible. There is no suggestion in the Butnaro patent of any steps that might be taken to reduce a user's perception of the cue lines, to avoid the distraction that they would cause while carrying out any other visual task. For example, if a user is attempting to watch a movie while a passenger on an aircraft, the Butnaro system would likely interfere with the enjoyment of the movie by overlaying the very visible and distracting cue lines on the visual input, thereby detracting from the scenes portrayed on the movie screen or other display. Butnaro's cue lines must be interpreted to determine the motion that has been sensed and require that a user be trained to interpret the motion and pay close attention. Accordingly, it appears that the user must directly "see" the cue lines to make the correct interpretation, or they will have little benefit. Intently watching a movie would interfere with the process of interpreting the cue lines if they are not so apparent, and the cue lines would thus provide little benefit.

No apparatus or technique is known that can provide an IVB truly corresponding to the sensations of a person's vestibular system that does not interfere with other visual tasks, or which can be controlled by a user, or which can provide a benefit for a plurality of people. The present invention addresses these issues.

SUMMARY OF THE INVENTION

In accord with the present invention, a method is defined for preventing a person from experiencing motion sickness. In one embodiment of the method, a motion experienced by the person is sensed, producing a signal indicative of the motion. The signal is processed so as to produce a modified signal that is compensated to correspond to a perception of the motion by the vestibular system of the person. Using the modified signal, an IVB is produced that includes visual cues matched to the perception of the motion by the vestibular system. This IVB tends to compensate for any mismatch between the visual perceptions of the person and the perception of motion by the person's vestibular system.

In one embodiment, the step of processing includes the step of employing a semicircular canal model to modify the signal to correspond to that of the vestibular system. In another embodiment, an otolith model is employed to modify the signal. In addition, the step of processing preferably includes the step of compensating the signal for the affects of individual differences in the perception of motion by the person's vestibular system.

For certain applications of the present invention, the step of displaying includes the step of projecting the IVB onto a surface that at least partially surrounds the person. Furthermore, the step of displaying can include the step of displaying a grid of lines comprising the visual cues that match the perception of the motion by the vestibular system. The grid of lines includes a first set of lines and a second set of lines, with the first set of lines being generally orthogonal to the second set of lines. Alternatively, the step of displaying the IVB may include the step of displaying a plurality of lines comprising the visual cues. In this embodiment, the plurality of lines match the perception of the motion by the vestibular system.

It is understood that the person may be engaged in an activity that involves a visual task, such as watching a motion picture in which considerable motion occurs. In this case, the step of displaying the IVB is implemented so as to limit a distracting affect of the IVB on the person while engaging in the visual task. Thus, it is preferable that the person be enabled to control one or more variables that affect the perceptibility of the IVB. These variables include an absolute or relative luminance of the IVB on the display, a relative position, extent, or size of the IVB, and a position at which the IVB appears relative to a position at which the visual task appears. Another controllable variable is a timing with which the display of the IVB occurs. For example, the control can be employed to modify a periodic time interval during which the IVB is repetitively displayed, an interval between successive periodic displays of the IVB, and/or a rate at which the IVB is periodically displayed. Yet other variables controllable by a user include a relative position, an extent, and a size on a display at which the IVB is displayed, either a focus of the IVB relative to a display or a depth of focus of the IVB in the space visually perceived by the person, a color of the IVB, and a color contrast of the IVB relative to a background on which it is displayed.

If the visual task comprises the step of viewing an image in which substantial motion is portrayed, the method preferably further includes the step of displaying the IVB so as to avoid obscuring the image.

In other applications of the present invention, the step of displaying includes the step of moving the visual cues about in a manner consistent with the perception of the motion by the vestibular system of the person.

The step of sensing motion preferably comprises the step of sensing at least one of a linear position, an angular position, a linear velocity, an angular velocity, a linear acceleration, and an angular acceleration, to which the person is subject. (It is noted that in most applications, six degrees of freedom will be sensed, although in certain applications, sensing three degrees of freedom can provide the signals necessary to fully implement the IVB.) When processing the signal, the step of modifying the signal is preferably carried out as a function of a first time constant and a second time constant. In this embodiment, the second time constant is substantially longer in duration than the first time constant.

Another aspect of the present invention is directed to a system for preventing a person from experiencing motion sickness due to a difference between a visual sensory perception and a vestibular system perception of motion. The system preferably includes a memory in which a plurality of machine instructions are stored, a display, and at least one motion sensor that produces an output signal indicative of motion. A processor, which is coupled to the memory, the display, and the one or more motion sensors, executes the plurality of machine instructions. These machine instructions cause the processor to carryout functions that are generally consistent with the steps of the method discussed above.

Still other aspects of the present invention are directed to a method and system for reducing an adverse physiological reaction caused by differences in a visually perceived motion and a lack of motion as sensed by the internal vestibular system of a person. In these aspects of the invention, a fixed IVB comprising visual cues substantially corresponding to and consistent with the lack of motion sensed by the internal vestibular system of the person is provided and displayed relative to an image depicting substantial motion that is being viewed by the person. The display of the IVB occurs without obscuring the image. The visual cues, which are consistent with the lack of motion perceived by the internal vestibular system of the person, substantially reduce an adverse physiological reaction that would be experienced by the person if the IVB were not displayed.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 2C illustrates an HMD that includes motion tracker and display screens on which a virtual environment is displayed along with an IVB;

FIG. 2D illustrates an example of a moving image virtual environment in which a variable perceptibility IVB is included in a central portion of the image;

FIG. 2E illustrates a pair of conventional glasses provided with a clip-on projector that produce an image of an IVB projected onto a user's retinas, so that the image appears to be focused in a plane in front of the user;

FIG. 5A is a schematic block diagram of a first mode of using an IVB to indicate a static, earth-fixed environment for a user viewing motion on an earth-fixed display, and which includes a user control for adjusting the noticeability or perceptibility of the IVB as required to avoid motion sickness;

Figure 8:
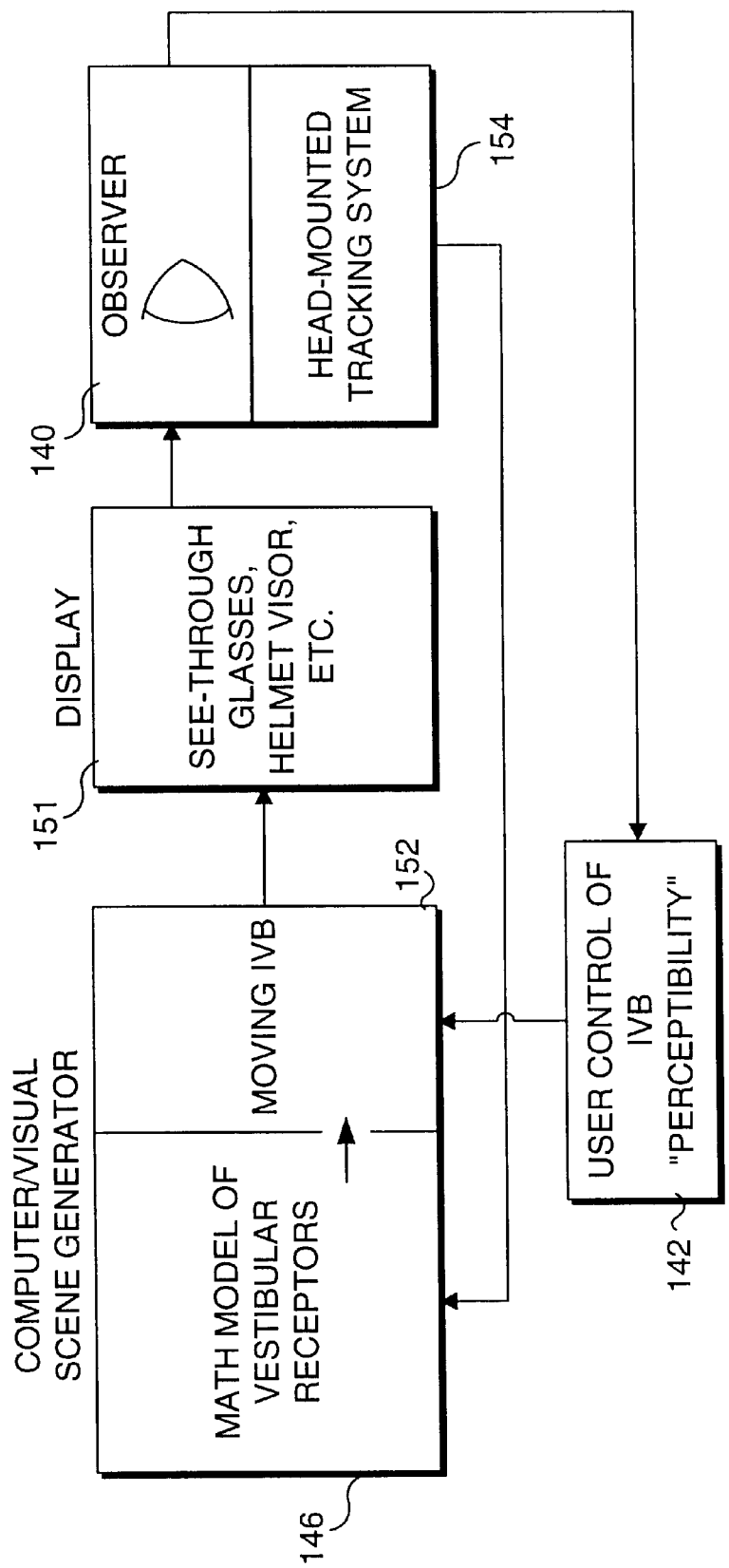
Figure 9:
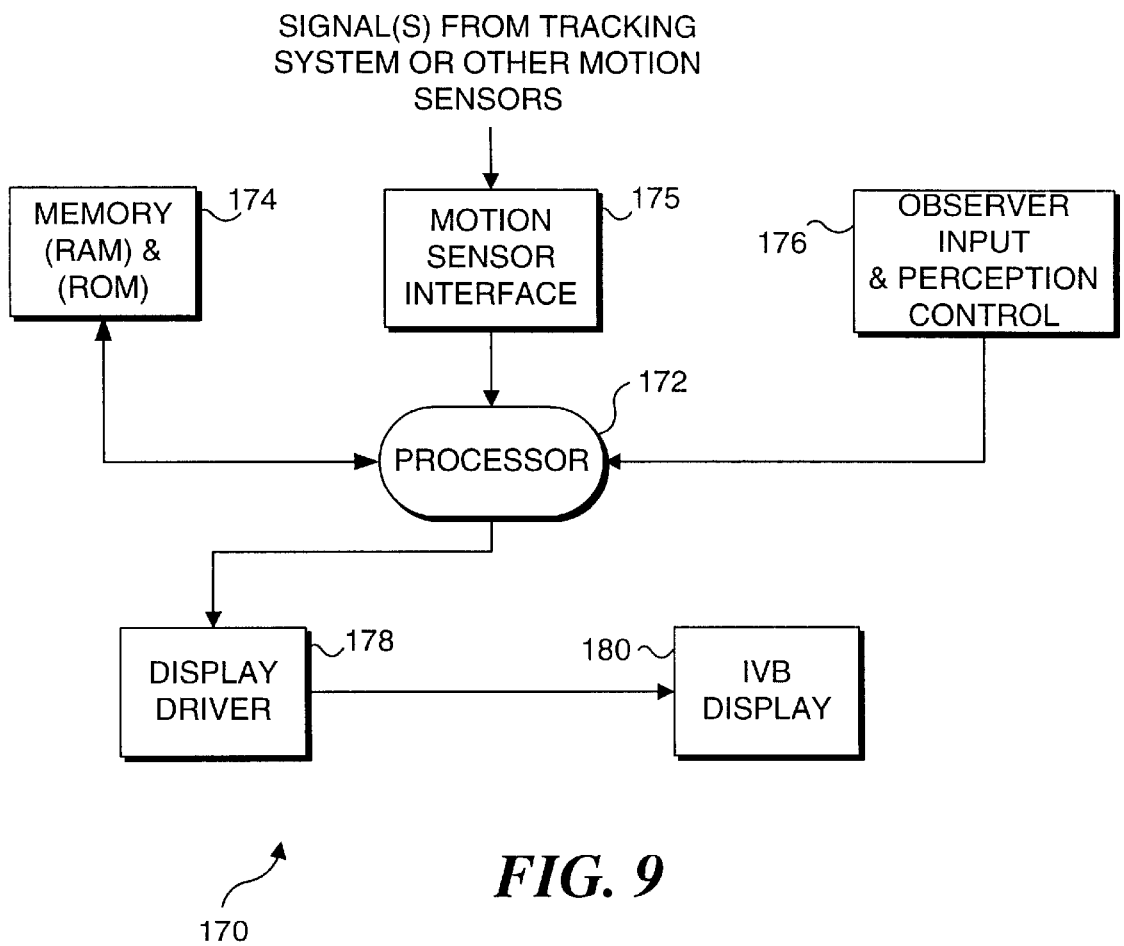

FIG. 8 is schematic block diagram of a fourth mode, for using an IVB in a moving (non-earth fixed) environment, with a head-fixed or mounted, see-through display, and with a control for enabling the user to adjust the perceptibility of the IVB; and FIG. 9 is a schematic block diagram of the components of a programmed processor system employed for producing the IVB and adjusting its perceptibility to the user.

DESCRIPTION OF THE PREFERRED EMBODIMENTS

Figure 1:
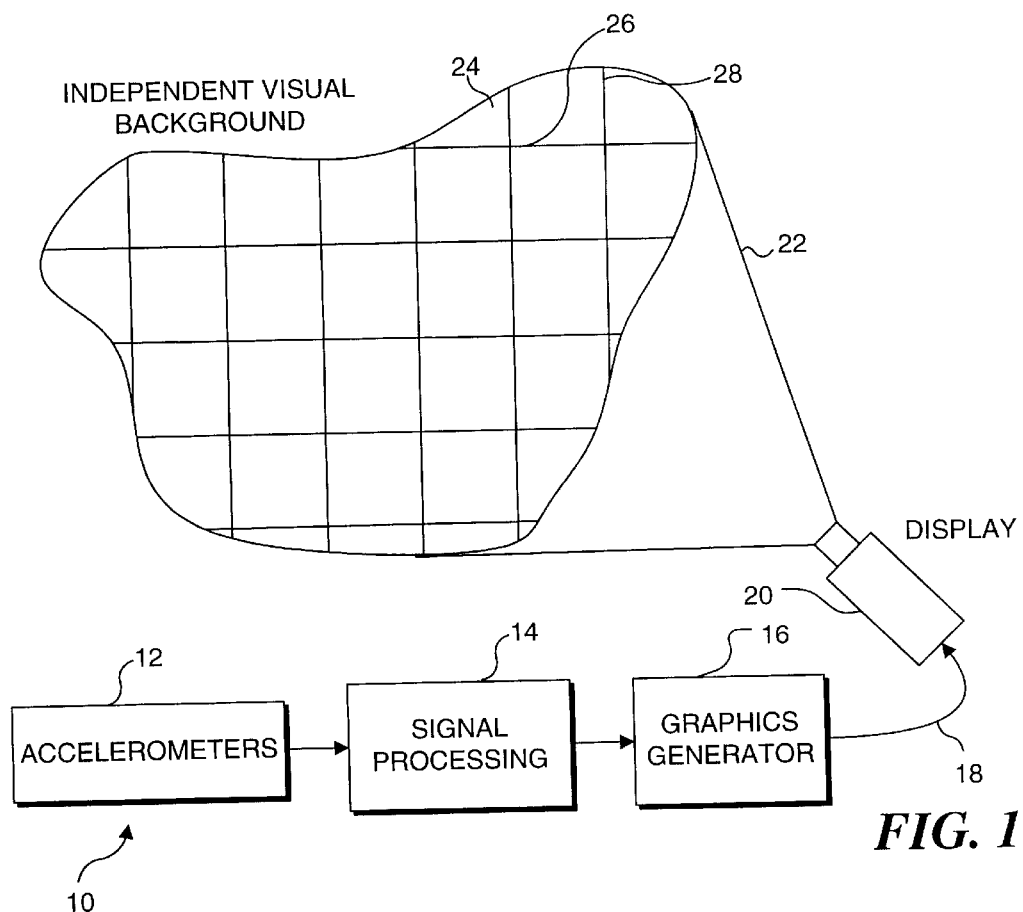
FIG. 1 is a schematic block diagram illustrating the functional components of the present invention that are employed to produce an IVB, which includes a grid.

As noted above in the Background of the Invention, motion sickness can be avoided by providing a person with a visual perception that matches the perception of motion produced by the vestibular system in the person's inner ear. Numerous tests have been conducted during the development of the present invention that demonstrate the benefit of providing a visual reference by displaying an IVB that includes visual cues comprising a plurality of lines oriented and moved about as necessary to represent motion corresponding to the motion experienced by the person's vestibular system. A system 10 for accomplishing this function is illustrated in FIG. 1 and preferably includes an inertial tracker 12 that detects motion of the person and/or of the environment in which the person is disposed. Inertial tracker 12 preferably senses six degrees of freedom, including three angular and three linear, relative to three orthogonal axes. One appropriate sensor for this purpose is the Model 600™ inertial motion tracker produced by Inner Sense Inc.

In some applications, it will be sufficient to sense fewer degrees of freedom. For example, if a person is riding on a boat or ship, three angular and one linear degrees of freedom would enable the present invention to display an IVB that provides visual cues corresponding to the heaving motion of the vessel and to the acceleration of gravity as perceived by the person's vestibular system. It should be understood that other motion-sensing devices, such as gyroscopes, magnetostrictive sensors, GPS receivers, etc. can alternatively be used for monitoring the motion of the user or of the environment in which the user is disposed. It is assumed that if the motion of the environment is monitored with such sensors, the user will be subject to the motion of the environment and will therefore sense the same motion monitored by the sensors. For example, motion sensors can be associated with a vessel, plane, vehicle or other type of conveyance carrying the user so that the velocity, acceleration, and gravity experienced by the conveyance while the conveyance moves, are also experienced by the user and are detected by accelerometers (and/or other sensors) 12. The motion sensing devices sense motion, including linear velocities and accelerations, and angular velocities and accelerations. The signal or signals produced by the motion-sensing devices such as accelerometers 12 are input to a signal processing component 14. As noted above, it is not sufficient to simply determine the acceleration and velocity to which a person is subjected, since the vestibular system does not respond to motion in the same manner as such sensors. Instead, signal processing component 14 is employed to modify the signals produced by the motion-sensing devices so that they correspond generally to the sensations or perceptions of the inner ear of a person subject to the motion.

At least one of two different models are proposed for use in processing the signal or signals produced by the motion sensors so that the modified signal or signals that are thus produced correspond to the sensations or perceptions of the person's inner ear. The first prospective model is the semicircular canal model for sensing angular motion, as described by the following equation:

$$\Phi/'A(s)=1/(T_1 s+1)(T_2 s+1) \qquad (1)$$

where $\Phi/'A(s)$ is the system gain, $T_1$ is a relatively short time constant (about 5 ms) and $T_2$ is a relatively long time constant (about 5 s). Alternatively, an otolith model for sensing linear motion and gravity can be employed for modifying the sensor signals and is described by the identical equation, but sets $T_1$ equal to about 330 ms and $T_2$ equal to about 10 to 20 s. Otolith ambiguity is handled in the following manner by the present invention. Given a signal from a linear motion sensor, a processor responds to the signal by moving the IVB so as to indicate either tilt with respect to gravity (rotation) or translation (straight-line motion). In an initial implementation of the present invention, the following rule is adopted. If signals indicative of motion are provided from both the linear and angular motion sensors, the IVB will be rotated. However, if signals indicative of motion are provided by the linear motion sensors, but not by the angular motion sensors, the IVB will be moved to indicate translation of the observer.

Either of the preceding models modify the signal produced by a motion sensor such as an accelerometer so that it generally corresponds to the perception of the person's vestibular system. It is also contemplated, however, that due to individual differences between people and the perceptions of their vestibular systems, it may be necessary to modify the time constants and/or other parameters of the models used to modify the signals so that the modified signals more closely correspond to the perceptions of a specific person's inner ear. For example, it is well known that as a person ages, the perception of their vestibular system changes. Similar changes occur as a consequence of abnormalities or illness. It is likely that further empirical data will be collected to more clearly determine how best to accommodate effects such as aging on the accuracy with which the perception of the vestibular system for a given individual is matched by the visual cues provided in the IVB so as to minimize or eliminate motion sickness experienced by a person.

The modified signal produced by signal processing component 14 is supplied to a graphics generator component 16, which produces an appropriate display signal such as a red, green, and blue (RGB) monitor drive signal, or a National Television Standards Committee (NTSC) signal, or a phase alternation line (PAL) signal, or a sequential couleur avec memoire (SECAM) signal, or other signal of the type commonly used for driving a monitor, television, or other display device. However, as discussed below, it is also expected that other types of graphic display devices be used for producing a display 20 that includes an IVB, in accord with the present invention. The signal supplied by graphics generator unit 16 is applied to produce display 20 that includes an IVB 24 as a projection 22. The IVB appears on a background surface, or is presented in another manner that is visible to the user.

In the illustrated example, IVB 24 is a grid that includes a plurality of nominally horizontal lines 26, which are substantially orthogonal to a plurality of nominally vertical lines 28. Preliminary empirical results have indicated that it is desirable to include a grid having five (5) or more of each type of line. However, it is possible that further testing will show that fewer or more lines are optimal for a given display surface, for preventing or minimizing the likelihood of a person experiencing motion sickness. It will be understood that IVB 24 is caused to move about in a manner that corresponds to the person's vestibular perception of motion. The motion of the IVB is made to correspond with the person's vestibular perception of motion by applying an appropriate model to the signals produced by the motion sensors.

It is important that the IVB provide a visual reference that accurately reflects how the person's inner ear perceives the motion to which the person is exposed. In other words, the IVB should move in a manner consistent with a person's expectations of the movement as determined by the person's perception of motion sensed by the inner ear. Thus, if the person's inner ear causes the person to feel like they are rolling to the right, IVB 24 should correspondingly rotate to the left at the same rate perceived by the person's vestibular system. The movement provided by IVB 24 that is received visually by the person will thereby match the expectations of the person based upon the perceptions of the person's vestibular system, and the person should not experience motion sickness.

Figure 1A:
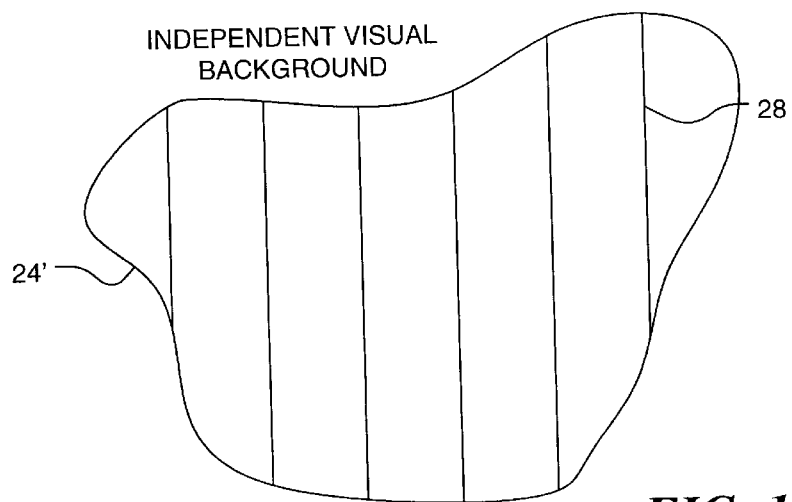
FIG. 1A is an alternative IVB comprising a plurality of generally parallel lines.

In addition, empirical testing has also determined that in certain limited applications of the present invention, the IVB can comprise either only nominally vertical or only nominally horizontal lines. FIG. 1A illustrates an IVB 24' comprising only nominally vertical lines 28. Of course, since the lines must move in a manner corresponding to the perceived motion by the person, it will be understood that the lines comprising the IVB will be caused to move and be oriented in a manner consistent with motion perceived by the person's vestibular system.

As explained above, a malady equivalent to motion sickness is often experienced by a person who is earth-fixed and not moving, but is watching a display or image in which motion is depicted. In this case, the input from the person's visual perception may cause the person to perceive that he/she is moving in a manner that fails to match the perceptions of the person's vestibular system, which senses that the person is not moving. The more pervasive the display in regard to the visually induced self-motion perception, e.g., a wrap-around screen in an IMAX™ theater, the greater will be the likelihood that the motion depicted thereon may lead to motion sickness.

Figure 2A:
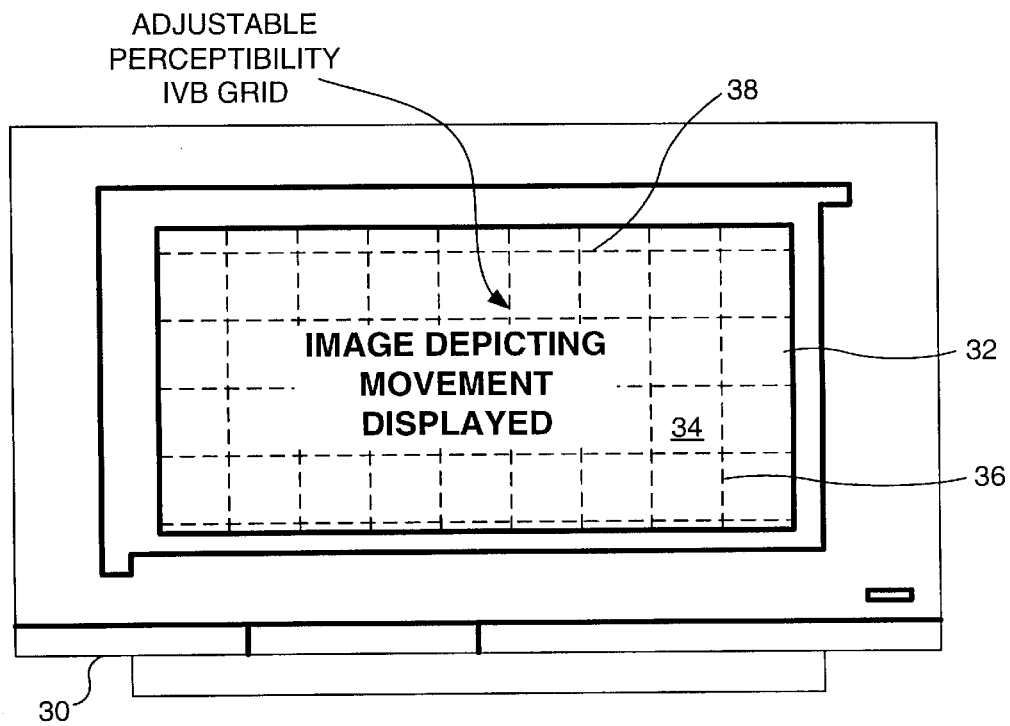
FIG. 2A is an elevational view of a monitor on which an adjustable perceptibility IVB is displayed over an image being viewed that includes substantial motion.

FIG. 2A illustrates a high-definition television monitor 30, having a display screen 32 with a length to height ratio of 16:9 is used for displaying an image 34 within which substantial movement is depicted. While it is possible that a person viewing image 34 could be doing so while in a moving conveyance, in most cases, the person will be in an earth-fixed state so that the person's vestibular system will not perceive any apparent motion of the person. Under such circumstances, since the person is not actually moving, but is viewing image 34 in which substantial motion is depicted, it is possible for the person to experience motion sickness because of the mismatch between the visual input and the perception of the person's inner ear. To prevent such motion sickness from being experienced, the present invention displays an earth-fixed IVB grid indicated in FIG. 2A as comprising dash lines 36 and 38. Since images on HDTV monitor 30 are often viewed in a semi-dark room, other visual cues such as the outline of furnishings that might provide the person with visual cues corresponding to the fixed perception of the vestibular system may not be readily apparent. Similarly, in an IMAX™ presentation, most of the visual field will be filled by a moving image and the person will not visually perceive fixed visual clues in the peripheral visual areas. Moreover, recent experimental data indicate than an IVB located in the periphery of the visual field is not as effective as one located more centrally. However, the IVB shown in this example provides a visually perceivable reference corresponding to the generally fixed perception of the vestibular system so that people viewing the presentations do not experience motion sickness. The fixed position IVB shown is also applicable to a wrap-around screen display.

To avoid potential problems or distractions caused by display of the IVB on the images being viewed, the person can be provided a control to adjust the perceptibility of the IVB, adjusting it to be only as perceptible as required to minimize the risk of or avoid experiencing motion sickness. The user can adjust the IVB perceptibility in regard to its absolute or relative luminance, making it less apparent by reducing the luminous intensity of lines 36 and/or lines 38 in the display, or can modify the relative depth at which the IVB appears in the visually perceived display so that it appears either behind or in front of the plane in which the image appears. This result can be achieved using the monocular depth cue of interposition and/or with a stereo image having apparent depth, due to retinal disparity. Alternatively, to minimize the perceptibility of the grid and any deleterious impact on the enjoyment of the images being displayed, the person can control the rate at which the IVB grid is displayed in an intermittent or flashing manner, or the duration of the successive displays of the IVB, or the time between each display of the IVB. Furthermore, the color of the IVB or the color contrast of the IVB can be varied to minimize the perceptibility of the IVB in regard to the images being displayed. It is also possible that user selection of certain colors will vary the effect of the IVB in preventing the person from experiencing motion sickness.

In each case in which the person controls the IVB perceptibility, the goal is to enable the person to reduce the extent to which the IVB is consciously noticed by a person to a level at which the IVB just accomplishes its desired effect in reducing or eliminating motion sickness that would otherwise be experienced. The person achieves this goal by varying one or more of the factors noted above. It is possible that the IVB can be controlled so that it is still possible to consciously perceive the IVB, if desired, and yet, the IVB will be displayed so that it will not be noticed by the person most of the time.

This visual perception effect is well known. For example, when wearing glasses, people generally do not consciously take notice of the frames or other portions of the glasses that are visually perceptible. A person will have ceased to take notice of such structural members of the glasses because they are not a part of the visual task to which the person is giving conscious attention. In the same fashion, it is likely that a person viewing an image or other visual task will not notice the IVB, even though if consciously desired, the person is still able to perceive it.

Figure 2B:
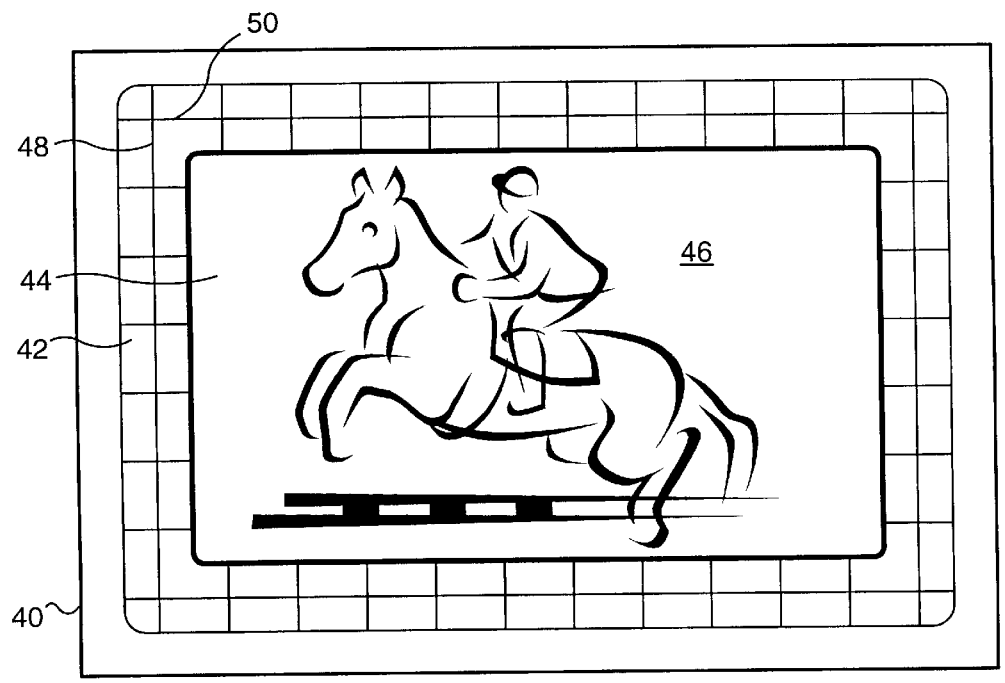
FIG. 2B is a display of an image that includes substantial motion and which includes a peripheral IVB formed around the borders of the image.

In FIG. 2B, another alternative is shown for displaying lines 48 and 50, which extend generally vertically and horizontally in a peripheral border 42 of a display monitor 40 and do not move or rotate. A display 44 illustrates an image 46 in which motion is depicted. However, a person viewing image 46 will also visually perceive lines 48 and 50 comprising an earth-fixed IVB grid and will therefore be provided with a visual reference that corresponds to the perceptions of the person's vestibular system, which indicate that the person is not moving. As a result, the person is generally much less likely to experience any motion sickness, since the lines provide the required reference that enables the visual perception to match that of the person's inner ear.

While monitors and display screens represent one approach for presenting an IVB to a person, it is also contemplated that various forms of HMDs can alternatively be used. HMDs are frequently employed for presenting the visual content of a virtual environment to a person or for displaying images in flight simulators and games in which the person is a participant. For example, FIG. 2C illustrates goggles 60 supported on the head of a person using a strap 64 on which a motion tracker 65 is mounted. Goggles 60 include a liquid crystal display (LCD) screen 66 on which are displayed moving images. A cable 62 extends to a display driver, which provides the signals employed to generate the images and is also used to generate the IVB. The person thus views images comprising, for example, scenes in a game or a virtual environment, or a motion picture in which movement occurs. Although the person is not in a moving environment and is typically in an earth-fixed environment, the person's head will move about, so motion tracker 65 is included to provide signals indicative of the motion of the person's head. However, the visual perceptions of the person viewing only the moving images will not match those of the vestibular system, and this mismatch can cause the person to experience motion sickness. To minimize or reduce the risk of motion sickness, the present invention provides for displaying an IVB within goggles 60, either peripherally around the images, or in a central portion of the display screen, or extending over the entire image on LCD screen 66. Again, the person has a control for adjusting the perceptibility of the IVB relative to the images comprising the visual task that is being viewed by the person. The IVB is moved about to correspond to the perception of motion by the person's vestibular system, responsive to movement of the person's head.

FIG. 2D provides an illustration of LCD screen 66 in which an image 68 of a sailboat is displayed moving along water. The IVB comprises a grid of lines 69 that are nominally horizontal and vertical and extend only within a central portion of image 68, moving about on the LCD screen in correspondence to the person's vestibular perception of motion due to movement of the person's head and/or movement of the environment in which the person is disposed. The person viewing image 68 is thus provided with an IVB generally matching the perception of the vestibular system due to motion of person's head. However, it is also contemplated that if the person is in motion, for example in an aircraft and is using goggles 60, the IVB comprising lines 69 will be moved about on LCD screen 66 in a manner consistent with and matching the vestibular perception of motion of the person, e.g., as a result of being within the moving aircraft and as a result of the motion of the head. Thus, if the aircraft were to bank to the left, lines 69 would be caused to rotate or tilt through a corresponding angle to the right so that the person perceives the expected visual change in the IVB in accord with the perception of the motion by the person that is provided by the person's vestibular system.

Yet another form of an HMD 70 is illustrated in FIG. 2E. In this embodiment of the present invention, the HMD is attached to ear pieces 73 on a pair of generally conventional glasses. The HMD includes a section 74, which is attached with clips 75 to ear pieces 73, and a projection section 72. Projection section 72 includes lenses 76 that project an image of an IVB 82 along a path 78 onto the retina (not shown) of the person so that the person sees an IVB 82 projected along a path in space a few feet in front of the person. The projected image directed into the retina follows path 78 so that the apparent projection appears as a projection 80 and in the example shown, comprises a grid of lines 84 that correspond to a portion of a wire-frame sphere. Thus, a person wearing glasses 79 is able to view the surrounding environment while being presented with the display of IVB 82 in which the person appears to be generally at a center of the sphere represented by the grid, and the grip is moved as appropriate to provide visual cues corresponding to the perceptions of the person's vestibular system. Glasses 79 still provide their normal corrective prescription, if any, or if the person has no need for corrected vision, they may comprise plain glass. Since sections 74 are held to ear pieces 73 with clips 75, the HMD can readily be removed when not required. However, since the HMD is relatively lightweight, and does not substantially interfere with the ability of the person to carry out regular visual tasks, which are visually perceived even when IVB 82 is projected, it will be apparent that the glasses can be worn on a continuous basis without significant disruption of regular activities in which the person engages. Thus, HMD 70 can be worn while the person is a passenger in a vehicle or other conveyance and is reading a book or engaged in other visual tasks, or can be worn while the person is in an earth-fixed disposition, but viewing a moving or moveable picture on a display. The signal to enable the projection of the IVB is provided by a display driver through cables 86, or alternatively, may be generated by processing circuitry included within the HMD.

Figure 3:
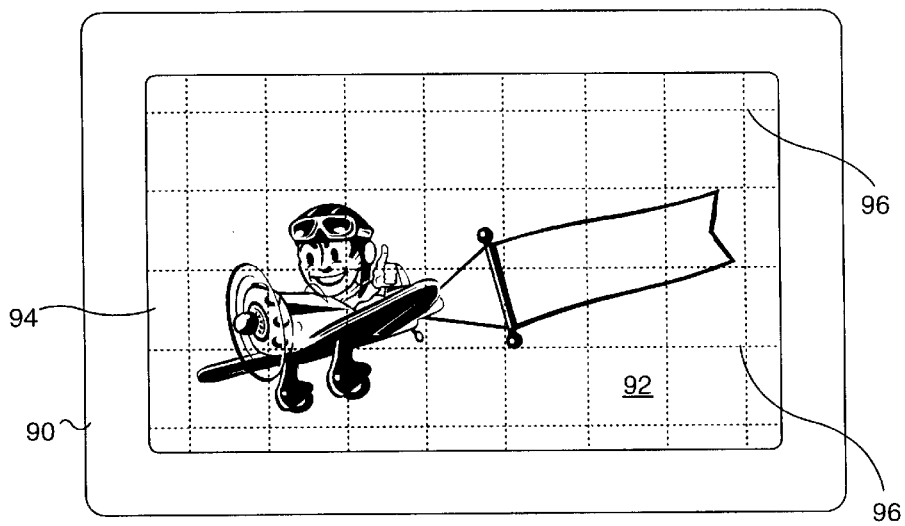
FIG. 3 is a schematic illustration of a moving image on a display in which the IVB is subliminally perceptible.

FIG. 3 illustrates yet another example in which a display 90 includes an image 92, which is presented on a screen 94. In this case, the IVB comprises a grid 96. In the simple example that is illustrated, image 92 is a cartoon character flying an aircraft. It is understood that motion of this type being depicted in a display is less likely to cause the person viewing the image to experience motion sickness. In contrast, if the image is a view as seen by the pilot while flying the aircraft, the likelihood of motion sickness is substantially increased. Accordingly, when the scene changes in this manner, lines 96 comprising the IVB that are barely or subliminally perceptible as shown in FIG. 3 can be made substantially more perceptible. The perceptibility of the IVB can thus be controlled in an automated manner by the display driver presenting the image as a function of the image being displayed and the likelihood that the image may cause motion sickness. Or alternatively, the person can be provided with a control to increase the perceptibility of the IVB when the likelihood of experiencing motion sickness increases because of the type of image being displayed. The control can simply be a push button switch that is engaged by the person when the image presented on display screen 94 changes to one more likely to cause motion sickness, and the person would use the switch to make the IVB less perceptible when the scene being displayed changes to an image less likely to cause motion sickness. It is also contemplated that some user's make desire to experience some degree of motion sickness and will choose to control the perceptibility of the IVB in a manner that enables the person to "enjoy" such an experience, without necessarily permitting the motion sickness to progress beyond a certain point.

Figure 4:
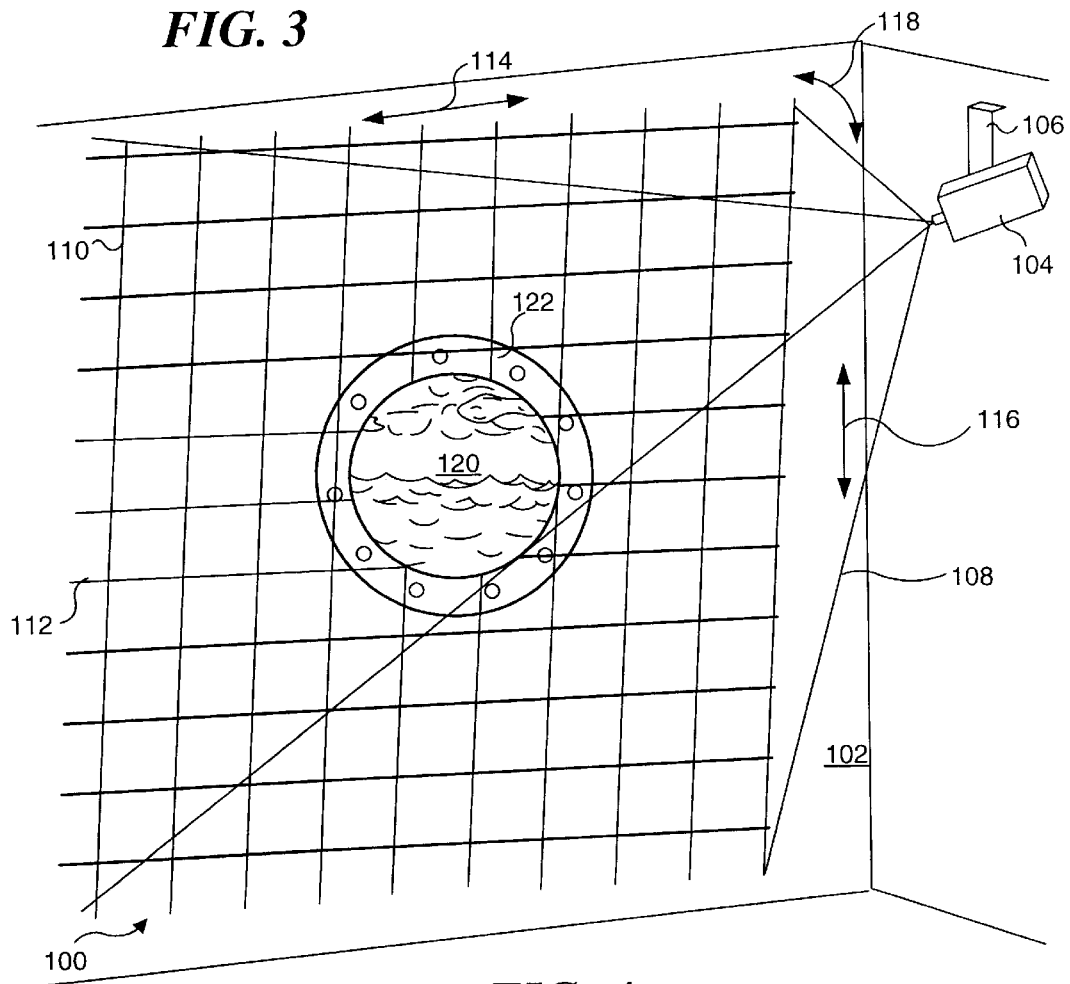
FIG. 4 is an isometric view of a cabin bulkhead (wall) on a ship, illustrating how the IVB is projected onto the surface to provide a visual reference for a plurality of people.

FIG. 4 illustrates yet another application of the present invention that is particularly useful when several people are in a moving environment. In this example, an IVB grid 100 comprises a projected image 108 formed by a projector 104 on a wall or other surface 102 of a surrounding environment. In the example shown, wall 102 comprises the bulkhead or wall of a cabin on a ship, as will be evident from a view 120 visible through a porthole 122. However, cabins on the interior of a large ship typically do not have the benefit of a porthole 122 to provide a view of the horizon, and thus, people who are enclosed within such a cabin are more likely to experience motion sickness as the ship rolls and pitches. To prevent such motion sickness, particularly when porthole 122 is not provided through which the outside horizon can be viewed, projector 104 projects IVB grid 100 comprising plurality of nominally vertical lines 110 and nominally horizontal lines 112, which move about and rotate in a manner that is consistent with the vestibular system of a person enclosed riding within the ship cabin and thus subject to its motion. Such a person will experience the motion of the ship with their vestibular system and it is important that a corresponding visual perception of that motion be provided by IVB grid 100 to avoid motion sickness. IVB grid 100 can shift generally horizontally, as indicated by an arrow 114, vertically as indicated by an arrow 116, or can rotate as indicated by an arc 118. Projector 104 is mounted with a bracket 106 to the enclosure, so that the disposition of IVB grid 100 and its relative movement on the wall or other surface 102 is controlled by the signal processing component, to correspond to the expected perceived motion sensed by the vestibular systems of one or more people within the cabin.

While only one projector 104 is illustrated, it will be understood that additional projectors can be provided, each projecting a corresponding IVB grid on other walls of the surrounding enclosure within which a person is disposed. Thus, the visual reference provided within the environment by the IVB grids projected on such surfaces should substantially eliminate motion sickness that might otherwise be experienced by people disposed within such an environment.

Turning now to FIG. 5A, the first of several different modes in which the present invention can be applied is illustrated. In this first example, it is presumed that the person employing the present invention is in a static earth-fixed environment and is viewing an earth-fixed display 138 which may employ a projector and dome, a screen, a wall, or other surface and may use a plurality of different projectors to display a moving or movable scene 134. The scene is controlled by either pre-programmed instructions or by the person using an input device such as a joystick, mouse, steering wheel, etc. Examples of such a moving/movable scene include images in games and virtual environments generated by a computer or other visual scene generator. Since it is assumed that the person is in a static, fixed environment, a static IVB 136 is also provided and included on display 138 within the visual perception of an observer 140. Observer 140 also is provided with a user control that determines the perceptibility of the IVB displayed to the person. Using this control, the observer can adjust the static IVB image so that it doesn't significantly distract the observer's attention from the moving or movable scene included on display 138. The control can be varied as the nature of the moving/movable scene changes, as necessary to avoid motion sickness.

Figure 5B:
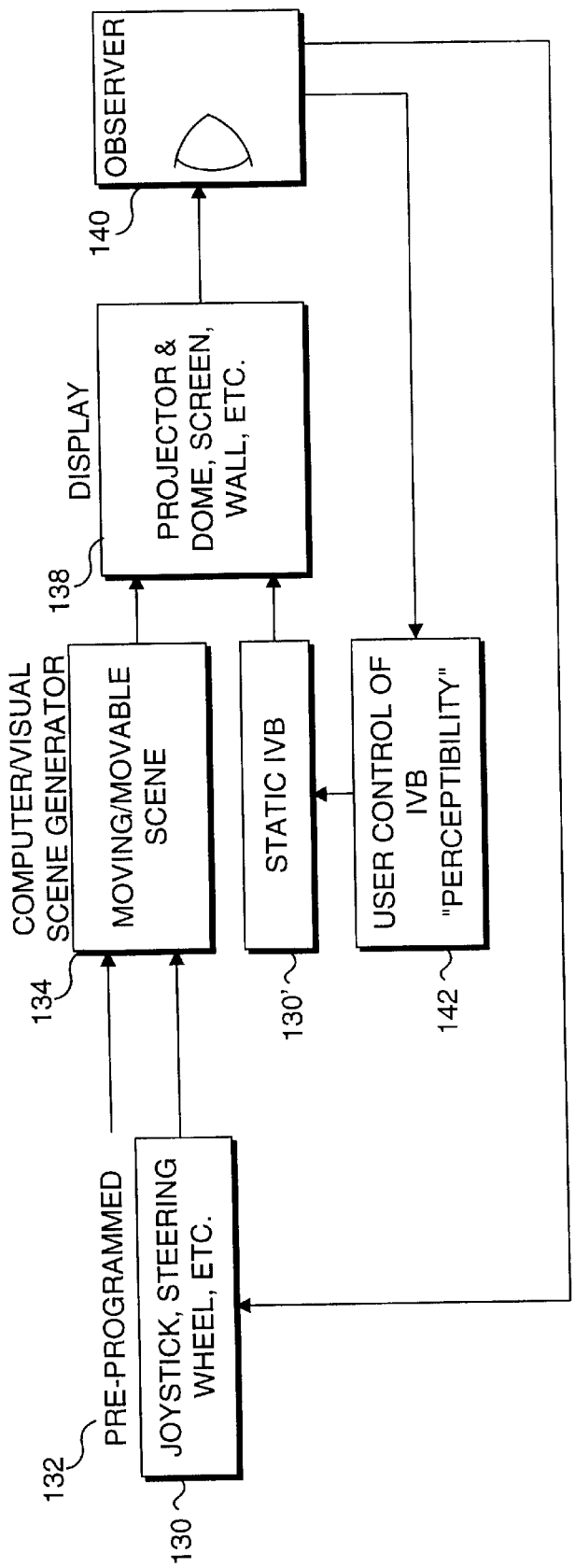
FIG. 5B is identical to FIG. 5A, except that a moving/movable scene and the IVB are generated by different systems rather than by a common system.

In FIG. 5B, substantially the same circumstances exist as described above in connection with FIG. 5A. However, in this Figure, it is contemplated that a static IVB 130' is generated by a computer or other visual scene generator separate from that providing moving/movable scene 134. Observer 140 still controls the perceptibility of the static IVB produced by this separate computer/visual scene generator. In all other respects, FIG. 5B is identical to FIG. 5A. In both of these examples, the IVB is intended to reduce or eliminate simulator/virtual environment sickness in motion simulators, IMAX™ theaters, and in other earth-fixed environment/earth-fixed display systems.

Figure 6:
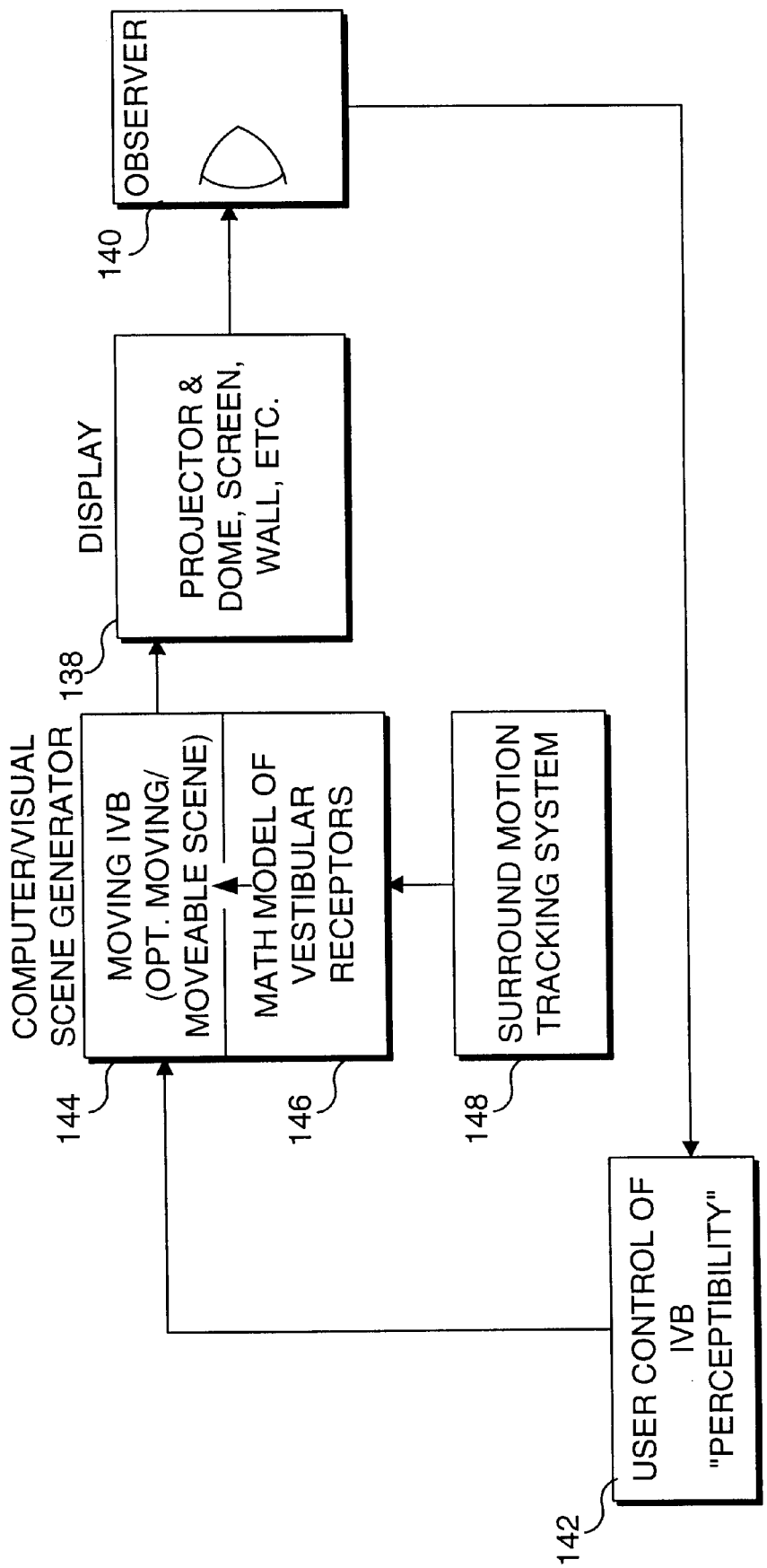
FIG. 6 is a schematic block diagram showing a second mode, for using an IVB in a moving environment (non-earth-fixed), displayed on an environment-fixed display, with a user control for adjusting the perceptibility of the IVB.

With reference to FIG. 6, a second mode of operation of the present invention is applicable in a moving or non-earth-fixed environment wherein display 138 is fixed within the moving environment. In this case, the orientation of the IVB and its motion on display 138 are controlled in response to the processed signal from a tracking system 148. The accelerometers or other motion sensors employed produce signals indicative of the motion of the environment that are supplied to a math model of the vestibular receptors of observer 140. The math model may be compensated specifically for individual characteristics of the vestibular receptors of that observer. Factors such as age and susceptibility to motion sickness can be employed in fine-tuning or tweaking the parameters used in the math model of the vestibular receptors. The modified signals are then employed to control the motion of IVB by the computer/visual scene generator. It is also contemplated that a moving or movable scene could be included, just as in FIGS. 5A and 5B, and that the scene can be either preprogrammed or controlled by user input. In this case, the composite of the moving IVB and the moving or movable scene would be presented on display 138. Observer 140 has the option of controlling the perceptibility of the IVB as necessary to avoid motion sickness and to minimize any distraction by the IVB from a moving or movable scene or other visual task being carried out by the observer. In the mode illustrated in FIG. 6, the IVB is intended to reduce motion sickness in a moving environment such as a ship, train, airplane, car, or other conveyance in which the observer is disposed.

Figure 7:
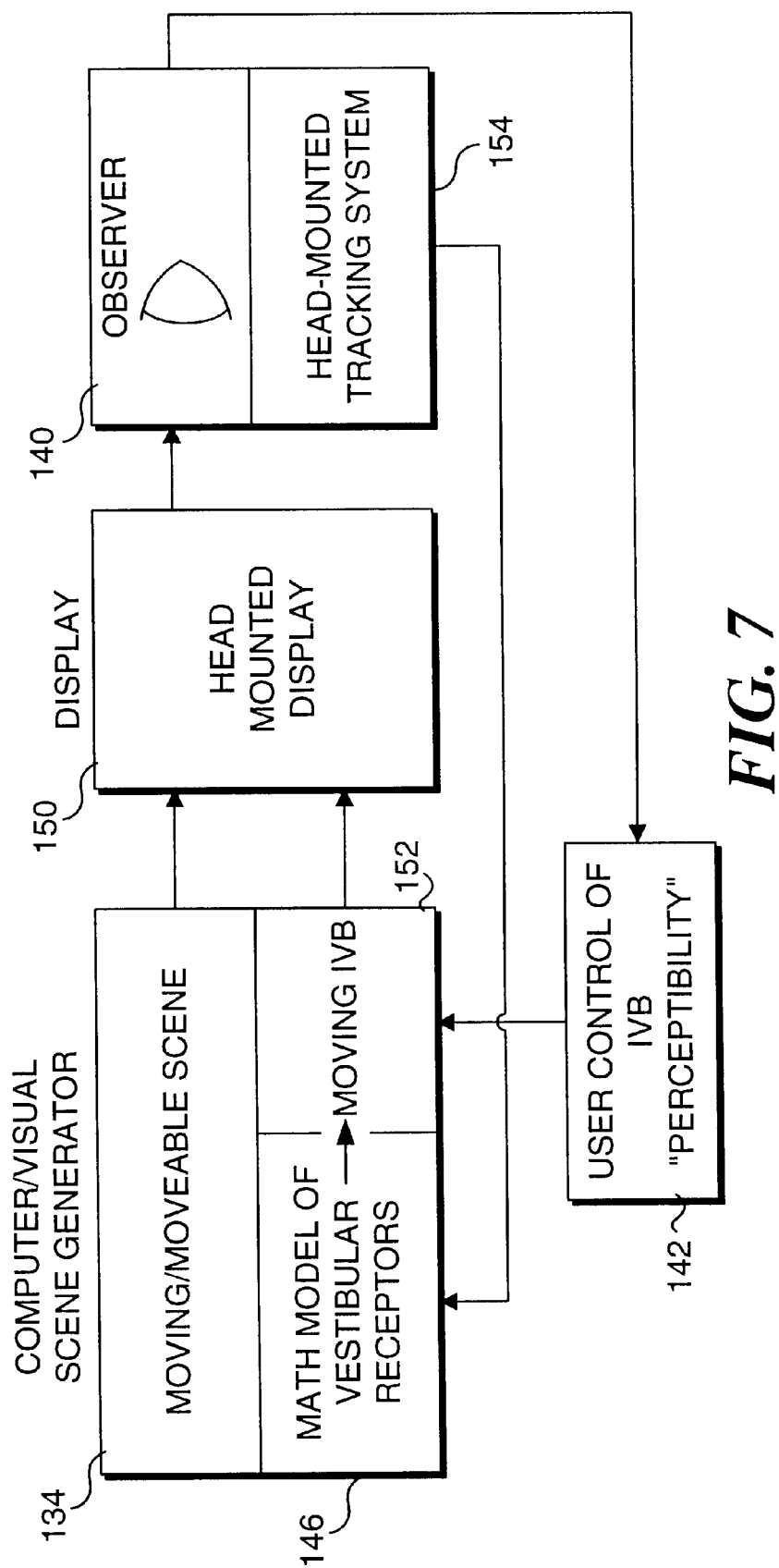
FIG. 7 is a schematic block diagram of a third mode, for using an IVB in a head-fixed, enclosed display, while in an earth-fixed environment, and with a user control for adjusting the perceptibility of the IVB.

FIG. 7 illustrates an application in which the observer is in an earth-fixed environment wearing a head-fixed HMD 150 (such as goggles 60, shown above in FIG. 2C). Since the display is head-fixed, it is important to track the motion of the observer's head, which can become significant as the observer becomes engrossed in the virtual environment, or game presented by HMD 150. Again, it is contemplated that a moving or movable scene will be presented within the display. However, the signals provided by head-mounted tracker/accelerometers 154 are supplied to a math model of vestibular receptors 146 to produce a moving IVB 152 that is presented on HMD 150. The user controls the perceptibility of the IVB in HMD 150 so that it does not interfere with the visual task represented by the moving/movable scene that is also displayed. However, the IVB is still sufficiently perceptible to minimize or substantially reduce the onset of motion sickness by observer 140. It is noted that HMD 150 is not a see-through type display, since the observer is totally enclosed visually within HMD 150. The perceptibility of the IVB display set by the observer will typically depend on the nature of moving/moveable scene 134 and/or the observer's physiological state and susceptibility to motion sickness. As presented in this example, the IVB is intended to reduce motion sickness resulting from playing video games, watching movies, participating in simulations such as flying or driving, and the display of other moving or movable scenes on HMD 150.

Finally, another application of the present invention is in a moving or non-earth-fixed environment wherein observer 140 is wearing a head-fixed see-through display 151 such as the HMD clipped to the glasses shown in FIG. 2E. Another example of such a display is a helmet visor on which moving IVB 152 is displayed. Signals from tracking system 154 are processed using math model of the vestibular receptors 146 of the observer so that moving IVB 152 can be produced with the display, enabling the observer to view the surrounding environment through the display, while benefiting from the moving IVB by avoiding motion sickness. An IVB can be adjusted by user control of perceptibility 142 so that it is relatively non-noticeable or is at a subliminal level, preventing the IVB from distracting the observer's attention from the surrounding environment. In addition, the adjustment of the IVB perceptibility will depend upon the nature of the environment in which the observer is disposed and the state of the observer and susceptibility to motion sickness. The example of this mode that is illustrated is intended to reduce motion sickness while an observer is engaged in normal activities in a moving environment, such as on a ship, car, or other vehicle or conveyance. Furthermore, this system provides protection against motion sickness without interfering with the performance of the observer in that moving environment. In a sense, the display of the IVB using see-through display means is analogous to the visual perception of the environment through sunglasses.

FIG. 9 illustrates details of a signal processor 170 that is used to implement a vestibular model to process the signals from a tracker/accelerometers or other motion sensors. A processor 172 is coupled to a memory 174, which includes both random access memory (RAM) and read only memory (ROM) in which machine instructions are stored. The machine instructions control the functionality of processor 172 when executed by it. In response to these machine instructions, processor 172 reads digital signals provided by a motion sensor interface 175, which converts the analog signals from the tracker/accelerometers or other motion sensors to a digital format. The machine instructions cause the processor to modify these digital signals so that they correspond to the response of an observer's vestibular system to motion. It should be noted that in the event that the observer is in an earth-fixed environment, motion sensor interface 175 can be omitted, since there is no need to process motion-related signals unless the observer is wearing a head-mounted tracker/accelerometer package that provides such signals.

A user input and perception control 176, which may comprise one or more controls for selectively controlling any of the parameters discussed above, such as absolute or relative luminance, repetition rate of successive IVB displays, duration of the repetitions, interval between displays, color, and color contrast of the IVB (relative to a background on which it is displayed) is coupled to processor 172 to enable the processor to respond to digital signals from motion sensor interface 175 and to the input provided by the user for controlling the perception of the IVB. Processor 172 provides an output signal in response to these input signals that is supplied to a display driver 178. The display driver produces an IVB display 180 in which the perceptibility of the IVB is adjusted in accord with the selected control input by the user and as necessary, the IVB is moved in response to the modified signals from the tracker/accelerometers in correspondence with the perceptions of the observer's vestibular system.

The signal processing component illustrated in FIG. 9 can be implemented using integrated circuit components, or can be embodied in an application-specific integrated circuit of sufficiently small size to fit within an HMD or other small enclosure. If incorporated within an HMD, there is no need for external processing devices, or graphic drivers, and leads to external devices are not required.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for preventing a person from experiencing motion sickness, comprising the steps of:
   (a) sensing a motion experienced by the person;
   (b) producing a signal indicative of said motion;
   (c) processing the signal so as to produce a modified signal that is compensated to correspond to a perception of the motion by the vestibular system of the person; and
   (d) using the modified signal, displaying an independent visual background that includes visual cues matched to the perception of the motion by the vestibular system.

2. The method of claim 1, wherein the step of processing comprises the step of employing a semicircular canal model to modify the signal.

3. The method of claim 1, wherein the step of processing comprises the step of employing an otolith model to modify the signal.

4. The method of claim 1, wherein the step of processing includes the step of compensating the signal for individual characteristics of the vestibular system of the person that affect the perception of motion.

5. The method of claim 1, wherein the step of displaying comprises the step of projecting the independent visual background onto a surface at least partially enclosing the person.

6. The method of claim 1, wherein the step of displaying the independent visual background comprises the step of displaying a grid of lines comprising the visual cues that match the perception of the motion by the vestibular system, said grid of lines including a first set of lines and a second set of lines, said first set of lines being generally orthogonal to said second set of lines.

7. The method of claim 1, wherein the step of displaying the independent visual background comprises the steps of:
   (a) displaying a plurality of lines comprising the visual cues; and
   (b) orienting the plurality of lines to match the perception of the motion by the vestibular system of the person.

8. The method of claim 1, wherein the person is engaged in an activity that involves a visual task, further comprising the step of displaying the independent visual background so as to limit a distracting affect of the independent visual background on the person.

9. The method of claim 8, wherein the person is enabled to control at least one of:
   (a) one of an absolute and a relative luminance of the independent visual background on the display;
   (b) a position at which the independent visual background appears relative to a position at which the visual task appears;
   (c) a timing with which the display of the independent visual background occurs, including at least one of:
      (i) a periodic time interval during which the independent visual background is repetitively displayed;
      (ii) an interval between successive periodic displays of the independent visual background;
      (iii) a rate at which the independent visual background is periodically displayed; and
      (iv) a duration of successive displays of the independent visual background;
   (d) one of a relative position, an extent, and a size at which the independent visual background is visually displayed;
   (e) one of a focus and a depth position of a focal point of the independent visual background;
   (f) a color of the independent visual background that is displayed; and
   (g) a color contrast of the independent visual background.

10. The method of claim 8, wherein the visual task comprises the step of viewing an image in which substantial motion is portrayed, further comprising the step of displaying the independent visual background so as to avoid obscuring the image.

11. The method of claim 1, wherein the step of displaying comprises the step of moving the visual cues about in a manner consistent with the perception of the motion by the vestibular system of the person.

12. The method of claim 1, wherein the step of sensing motion comprises the step of sensing at least one of a linear position, an angular position, a linear velocity, an angular velocity, a linear acceleration, and an angular acceleration.

13. The method of claim 1, wherein the step of processing includes the step of modifying the signal as a function of a first time constant and a second time constant, said second time constant being substantially longer in duration than the first time constant.

14. The method of claim 1, wherein the step of sensing comprises the step of sensing both an angular and linear motion, and wherein the step of processing includes the step of modifying the signal to resolve an otolith ambiguity, wherein if both linear and angular motions are sensed, the independent visual background is rotated, and if the only linear motion is sensed, but not angular motion, the independent visual background is moved to indicate a translation of the person.

15. The method of claim 1, wherein the step of displaying includes the step of displaying the independent visual background so that it is visible to a plurality of people who are subject to a substantially common motion.

16. A system for preventing a person from experiencing motion sickness due to a difference between a visual sensory perception and a vestibular system perception of motion, comprising:
   (a) a memory in which a plurality of machine instructions are stored;
   (b) a display;
   (c) at least one motion sensor that produces an output signal indicative of motion; and
   (d) a processor coupled to the memory, the display, and said at least one motion sensor, said processor executing the plurality of machine instructions, causing the processor to:
      (i) process the signal, producing a modified signal that is compensated to correspond to a perception of the motion by the vestibular system of the person; and
      (ii) using the modified signal, display an independent visual background that includes visual cues matched to the perception of the motion by the vestibular system.

17. The system of claim 16, wherein the plurality of machine instructions further cause the processor to implement a semicircular canal model to modify the signal.

18. The system of claim 16, wherein the plurality of machine instructions further cause the processor to implement an otolith model to modify the signal.

19. The system of claim 16, wherein the plurality of machine instructions further cause the processor to compensate the signal for any affects of aging of the person.

20. The system of claim 16, wherein the display comprises a projector that projects the visual cues comprising the independent visual background onto a surface at least partially surrounding the person.

21. The system of claim 16, wherein the display comprises a projector that projects the visual cues comprising the independent visual background onto a surface worn by the person.

22. The system of claim 16, wherein the display is adapted to mount on a head of a person and to project the visual cues onto a retina of the person.

23. The system of claim 16, wherein the visual cues of the independent visual background comprise a grid of lines that are oriented to match the perception of the motion by the vestibular system, said grid of lines including a first set of lines and a second set of lines, said first set of lines being generally orthogonal to said second set of lines.

24. The system of claim 16, wherein the visual cues of the independent visual background comprise a plurality of lines that are oriented to match the perception of the motion by the vestibular system.

25. The system of claim 16, wherein the person is engaged in an activity that involves a visual task, said machine instructions further causing the processor to display the independent visual background with the display so as to reduce a distracting affect of the independent visual background on the person.

26. The system of claim 16, further comprising a control that is coupled to one of the processor and the display, said control enabling a person to control an extent to which the visual cues of the independent visual background are visually perceptible on the display.

27. The system of claim 25, wherein the control varies at least one of:
   (a) a luminance of the independent visual background on the display;
   (b) a position at which the independent visual background appears relative to a position at which the visual task appears;
   (c) a timing with which the display of the independent visual background occurs, including at least one of:
      (i) a periodic time interval during which the independent visual background is repetitively displayed;
      (ii) an interval between successive periodic displays of the independent visual background;

(iii) a rate at which the independent visual background is periodically displayed; and
(iv) a duration of successive displays of the independent visual background;
(d) a relative position at which the independent visual background is visually displayed;
(e) one of a focus and a depth focal point of the independent visual background in a visually perceptible space of a person;
(f) a color of the independent visual background that is displayed; and
(g) a color contrast of the independent visual background.

28. The system of claim 26, wherein the visual task pertains to viewing an image in which substantial motion is portrayed, said machine instructions further causing the processor to provide the independent visual background on the display in a manner that does not obscure the image.

29. The system of claim 16, wherein the machine instructions further cause the process to move the visual cues consistent with the perception of the motion by the vestibular system of the person.

30. The system of claim 16, wherein said at least one sensor comprises at least one of:
(a) a linear position sensor;
(b) an angular position sensor;
(c) a linear velocity sensor;
(d) an angular velocity sensor;
(e) a linear acceleration sensor; and
(f) an angular acceleration sensor.

31. The system of claim 16, wherein the machine instructions further cause the processor to modify the signal as a function of a first time constant and a second time constant, said second time constant being substantially longer in duration than the first time constant.

32. A method for reducing an adverse physiological reaction caused by differences in a visually perceived motion and a lack of motion as sensed by the internal vestibular system of a person, comprising the steps of:
(a) providing a fixed independent visual background comprising visual cues substantially corresponding to and consistent with the lack of motion sensed by the internal vestibular system of the person; and
(b) displaying the fixed independent visual background relative to an image depicting substantial motion that is being viewed by the person, without obscuring the image, said visual cues, which are consistent with the lack of motion perceived by the internal vestibular system of the person, substantially reducing an adverse physiological reaction that would be experienced by the person if the independent visual background were not displayed.

33. The method of claim 32, further comprising the step of enabling a person to control an extent to which the visual cues comprising the independent visual background are perceptible relative to the image, in order to enable the person to set the extent sufficiently to substantially control the adverse physiological reaction.

34. The method of claim 32, wherein the step of displaying comprises the step of displaying visual cues, said visual cues comprising a first set of lines and a second set of lines, said second set of lines being substantially orthogonal to the first set of lines.

35. The method of claim 32, wherein the step of displaying comprises the step of displaying visual cues, said visual cues comprising at least one of:
(a) a plurality of substantially parallel lines; and
(b) a plurality of lines corresponding to at least a portion of a spherical surface.

36. The method of claim 32, wherein the step of displaying comprises the step of displaying line segments around a periphery of the image.

37. The method of claim 32, wherein the step of displaying comprises the step of displaying visual cues that overlie the image, said visual cues being sufficiently diffuse so as not to obscure the image.

38. The method of claim 32, wherein the step of displaying comprises the step of displaying visual cues that overlie the image, but are at a different focal point within a visually perceptible space of the person, so as not to obscure the image.

39. The method of claim 32, further comprising the step of displaying the visual cues comprising the independent visual background as a subliminal image that is not consciously perceptible.

* * * * *